United States Patent
Herr et al.

(10) Patent No.: US 11,864,567 B2
(45) Date of Patent: Jan. 9, 2024

(54) METHODS AND FORMULATIONS FOR REDUCING BOVINE EMISSIONS

(71) Applicant: Elanco US Inc., Greenfield, IN (US)

(72) Inventors: Cory T. Herr, Greens Fork, IN (US); John Charles Kube, Greenfield, IN (US); Jerold Scott Teeter, Greenfield, IN (US)

(73) Assignee: ELANCO US INC., Greenfield, IN (US)

(*) Notice: Subject to any disclaimer, the term of this patent is extended or adjusted under 35 U.S.C. 154(b) by 5 days.

(21) Appl. No.: 17/724,717

(22) Filed: Apr. 20, 2022

(65) Prior Publication Data

US 2022/0240545 A1 Aug. 4, 2022

Related U.S. Application Data

(63) Continuation of application No. 15/514,876, filed as application No. PCT/US2016/055123 on Oct. 3, 2016, now Pat. No. 11,344,047, which is a continuation-in-part of application No. PCT/US2015/054040, filed on Oct. 5, 2015.

(51) Int. Cl.

| A23K 20/121 | (2016.01) |
|---|---|
| A23K 20/111 | (2016.01) |
| A23K 20/132 | (2016.01) |
| A23K 20/195 | (2016.01) |
| A23K 50/10 | (2016.01) |
| A23K 20/184 | (2016.01) |
| A23K 10/40 | (2016.01) |
| A23K 10/00 | (2016.01) |

(52) U.S. Cl.
CPC ............ *A23K 20/111* (2016.05); *A23K 10/40* (2016.05); *A23K 20/121* (2016.05); *A23K 20/132* (2016.05); *A23K 20/184* (2016.05); *A23K 20/195* (2016.05); *A23K 50/10* (2016.05); *A23K 10/00* (2016.05); *A23V 2002/00* (2013.01)

(58) Field of Classification Search
CPC ... A23K 20/111; A23K 20/121; A23K 20/132
See application file for complete search history.

(56) References Cited

U.S. PATENT DOCUMENTS

| 5,480,908 | A | 1/1996 | Epstein et al. | |
|---|---|---|---|---|
| 6,730,792 | B2 | 5/2004 | Evers et al. | |
| 6,790,792 | B2 * | 9/2004 | Shaffer, II | H01L 23/49894 257/E23.077 |
| 11,344,047 | B2 * | 5/2022 | Herr | A23K 50/10 |
| 2015/0203471 | A1 | 7/2015 | Aissat et al. | |

FOREIGN PATENT DOCUMENTS

CN 1441800 A 9/2003

OTHER PUBLICATIONS

Walker, C.E., et al. "Effects of Ractopamine Hydrochloride are not Confined to Mammalian Tissue: Evidence for Direct Effects of Ractopamine Hydrochloride Supplementation on Fermentation by Ruminal Microorganisms." J. Animal Sciences. (2010), vol. 88, pp. 697-706. (Year: 2010).*
"FDA Approves Experior for Reduction of Ammonia Gas Released from Beef Cattle Waste." (Nov. 6, 2018). Accessed Sep. 2, 2019. (Year: 2018).*
Goodman, Scott. "Pharmacology Test 1 Drug List." (1999). Accessed Sep. 2, 2019. pp. 1 of 24 through 24 of 24. Available from: < https://www.kumc.edu/AMA-MSS/Study/pharm1_table.htm >. (Year: 1999).*
European Medicines Agency. "Monensin: Committee for Medicinal Products for Veterinary Use." (2007), pp. 1-9 of 9. (Year: 2007).*
European Medicines Agency. "Tylosin: Committee for Medicinal Products for Veterinary Use." (Apr. 1997), pp. 1-8 of 8. (Year: 1997).*
Herrman, Tim, et al. "Medicated Feed Additives for Beef Cattle." Beef Cattle Handbook. (Jun. 26, 2016), pp. 1-9 of 9. (Year: 2016).*
Thomson Scientific WPI, Abstract NL2002197C (JOZ BV) XP-002752309, (May 17, 2010).
Thomson Scientific WPI, Abstract NL1006953C (Agritech) XP-002785310, (Mar. 8, 1999).
Thomson Scientific WPI, Abstract NL9300228A (Agrobiologisch Onderzoek) XP-002752311, (Sep. 1, 1994).
International Search Report of International Application No. PCT/US2016/055123, dated Jan. 19, 2017.
Written Opinion of the International Searching Authority of International Application No. PCT/US2016/055123, dated Jan. 19, 2017.
Stackhouse-Lawson et al., "Growth promoting technologies reduce greenhouse gas, alcohol, and ammonia emissions from feedlot cattle", J ANIN SCI 2013, 91:5438-5447.
Walker, C.E. et al., "Effects of Ractopamine Hydrochloride are not Confined to Mammalian Tissue: Evidence for Direct Effects of Ractopamine Hydroclordie Supplementation on Fermentation by Ruminal Microoganiams", J. Animal Science 2010; 88:697-706, Doi: 10/2527/ jas.2009-1000.
U.S. Food and Drug Administration, "FDA Approves Experior for Reduction of Ammonia Gas Released from Beef Cattle Waste."(Nov. 6, 2018). Accessed Sep. 2, 2019. (Year 2018).
Goodman, Scott, "Pharmacology Test 1 Drug List." (1999). Accessed Sep. 2, 2019, pp. 1 0f 24 throuh 24 of 24. Available from: https://www.kumc.edu/AMA-MSS/Study/pharm1_table.htm. (year: 1999).

* cited by examiner

*Primary Examiner* — John S Kenyon

(74) *Attorney, Agent, or Firm* — McBee Moore & Vanik IP, LLC

(57) ABSTRACT

The present disclosure provides methods and formulations for reducing ammonia and carbon dioxide emissions from a bovine using lubabegron, or a physiologically acceptable salt thereof. The present disclosure also provides bovine feed additives and bovine feed compositions.

6 Claims, No Drawings

METHODS AND FORMULATIONS FOR REDUCING BOVINE EMISSIONS

CROSS-REFERENCE TO RELATED APPLICATIONS

This patent application is a continuation of U.S. patent application Ser. No. 15/514,876, filed Mar. 28, 2017, which is a national stage entry of International Patent Application No. PCT/US2016/055123, filed 3 Oct. 2016, which is a continuation-in-part of International Patent Application No. PCT/US2015/054040, filed 5 Oct. 2015, the contents of which are herein incorporated in their entirety.

Ammonia is the most abundant alkaline gas in the atmosphere. In addition, it is a major component of total reactive nitrogen. Recent studies have indicated that ammonia emissions have been increasing over the last few decades on a global scale. This is a concern because ammonia plays a significant role in the formation of atmospheric particulate matter, visibility degradation and atmospheric deposition of nitrogen to sensitive ecosystems. Additionally, carbon dioxide is a greenhouse gas linked to global warming. Thus, the increase in ammonia and carbon dioxide emissions negatively influences environmental and public health. Bovines, and particularly cattle, are major emitters of ammonia and contribute significantly to carbon dioxide emissions. Ammonia is generated and emitted by bovines during their digestive process, as well as emitted from bovine wastes as they break down.

Different approaches have been used to control ammonia and carbon dioxide emissions from bovines. One set of methods for reducing ammonia and carbon dioxide emissions are dietary manipulation strategies. One such approach applied to reducing both ammonia and carbon dioxide emissions is to reduce the amount of protein fed to the bovine. However, such a lower protein approach can lead to lesser amounts or slower accumulation of desired bovine muscle. In addition to dietary manipulation strategies, many other practices have been utilized for reducing ammonia emissions, such as filtration of emissions and particles, building impermeable barriers to prevent the movement of ammonia emissions, and control strategies for feces and urine in bovine raising operations. Many of these practices are costly, inconvenient, and of limited benefit. Therefore, there exists a need for alternatives for reducing bovine ammonia and carbon dioxide emissions. Preferably, such alternatives decrease the inconvenience, drawbacks, and/or cost of one or more of the current approaches.

U.S. Pat. No. 6,730,792 ('792) discloses lubabegron and salts thereof for use in treating Type II diabetes and obesity and for binding to and activating the $\beta_3$ receptor. Additionally, '792 states that in non-human, non-companion animals, the compounds of formula I described therein are useful for increasing weight gain and/or improving the feed utilization efficiency and/or increasing lean body mass and/or decreasing birth mortality rate and increasing post/natal survival rate. However, lubebagron or salts thereof was not known to reduce ammonia and/or carbon dioxide emissions from bovine.

The present invention provides a method of reducing ammonia and/or carbon dioxide emissions from a bovine in need thereof comprising orally administering to the bovine lubabegron, or a physiologically acceptable salt thereof.

Another aspect of the present disclosure provides lubabegron, or a physiologically acceptable salt thereof, for use in reducing ammonia and/or carbon dioxide emissions from a bovine.

Another aspect of the present disclosure provides lubabegron, or a physiologically acceptable salt thereof, for use in reducing ammonia and/or carbon dioxide emissions from a bovine wherein said lubabegron is to be orally administered.

Another aspect of the present disclosure provides a bovine feed additive which comprises lubabegron, or a physiologically acceptable salt thereof, and a suitable carrier therefor, wherein said additive is for the reduction of ammonia and/or carbon dioxide emissions.

Another aspect of the present disclosure provides an animal feed for reducing ammonia and/or carbon dioxide emissions from a bovine which comprises a bovine feed and lubabegron, or a physiologically acceptable salt thereof.

Lubabegron, or a physiologically acceptable salt thereof, such as lubabegron fumarate, may be made by processes known in the art. The hemifumarate salt of lubabegron is known as lubabegron fumarate (CAS Registry Number 391926-19-5). For example, the processes described in U.S. Pat. No. 6,730,792 are illustrative processes that may be used to make lubabegron, or a physiologically acceptable salt thereof.

As used herein, the term "bovine" refers to an animal that is a member of the biological subfamily Bovinae, including but not limited to cows/cattle, bison, African buffalo, and water buffalo. In preferred embodiments, the animal is a cow. As used herein, the term "cow" is a bovine of either sex or age, and is a member of the biological genus Bos, including the species Bos taurus and Bos indicus. Cows in a group are commonly known as cattle. As such, the term cow includes dairy cattle, beef cattle, bulls, heifers, oxen, and steers.

As used herein, "reducing ammonia emissions" from a bovine treated with lubabegron, or a physiologically acceptable salt thereof, refers to reducing emitted ammonia gas relative to a bovine not treated with lubabegron, or a physiologically acceptable salt thereof. In some embodiments, the reduction is from about 10 to about 30% in ammonia emissions when compared to an untreated animal. In some embodiments, the reduction is from about 15 to about 25% in ammonia emissions. In some embodiments, the reduction of ammonia emissions from a bovine does not significantly negatively affect the bovine, such as, for example, lowering body weight, or decreasing meat and eating quality. In some embodiments, the reduction is per pound of live weight of the bovine. Live weight means the weight of the bovine while alive. In some embodiments, the reduction is per pound of hot carcass weight of the bovine. Hot carcass weight is the weight of a bovine carcass prior to chilling with its hide, head, gastrointestinal tract, and internal organs removed. In some embodiments, the reduction of ammonia is accompanied by an increase in hot or live carcass weight. In some embodiments, the bovine is in confinement for slaughter when administered lubabegron, or a physiologically acceptable salt thereof.

As used herein, "reducing carbon dioxide emissions" from a bovine treated with lubabegron, or a physiologically acceptable salt thereof refers to reducing emitted carbon dioxide gas relative to a bovine not treated with lubabegron, or a physiologically acceptable salt thereof. In some embodiments, the reduction is about 9% in carbon dioxide emissions when compared to an untreated animal when carbon dioxide emissions are standardized to animal live weight. In some embodiments, the reduction is about 10% in carbon dioxide emissions when compared to an untreated animal when carbon dioxide gas emissions are standardized by animal hot carcass weight. In some embodiments, the reduction of carbon dioxide emissions from a bovine does not significantly negatively affect the bovine, such as, for example, lowering body weight, or decreasing meat and eating quality. In some embodiments, the reduction is per pound of live weight of the bovine. Live weight means the weight of the bovine while alive. In some embodiments, the reduction is per pound of hot carcass weight of the bovine. Hot carcass weight is the weight of a bovine carcass prior to chilling with its hide, head, gastrointestinal tract, and internal organs removed. In some embodiments, the reduction of carbon dioxide is accompanied by an increase in hot or live carcass weight. In some embodiments, the bovine is in confinement for slaughter when administered lubabegron, or a physiologically acceptable salt thereof. Lubabegron, or a physiologically acceptable salt thereof, can be formulated for oral administration, and such formulations include animal feeds and feed additives. In some embodiments, the administration is carried out by including lubabegron, or a physiologically acceptable salt thereof, in an animal (bovine) feed. The animal feed may be a dry feed or a liquid feed, and includes a bovine's drinking water containing lubabegron, or a physiologically acceptable salt thereof. Such animal feeds may include lubabegron, or a physiologically acceptable salt thereof, combined or admixed with suitable feedstuffs commonly employed in the feeding of bovines. Typical feedstuffs commonly employed include corn meal, corncob grits, soybean meal, alfalfa meal, rice hulls, soybean mill run, cottonseed oil meal, bone meal, ground corn, corncob meal, wheat middlings, limestone, dicalcium phosphate, sodium chloride, urea, distillers dried grain, vitamin and/or mineral mixes, cane molasses or other liquid carriers and the like. Such feedstuffs promote a uniform distribution and administration of lubabegron, or a physiologically acceptable salt thereof. In some embodiments, feedstuffs containing lubabegron, or a physiologically acceptable salt thereof, is provided to a bovine ad libitum (i.e., "at will").

While a particular embodiment for orally administering lubabegron, or a physiologically acceptable salt thereof, is via daily feed rations, lubabegron, or a physiologically acceptable salt thereof, can be incorporated into salt blocks and mineral licks, as well as being added directly to lick tank formulations or drinking water for convenient oral consumption. Lubabegron, or a physiologically acceptable salt thereof, can also be administered orally by bolus or gavage treatment.

In some embodiments, feed additives are provided which include lubabegron, or a physiologically acceptable salt thereof, and one or more suitable carriers. The feed additive may be a dry feed additive or a liquid feed additive. The feed additives are formulated such that, when added with other materials, an animal feed is formed which will provide a desired concentration of lubabegron, or a physiologically acceptable salt thereof, in the animal feed, and/or provide the desired dose of lubabegron, or a physiologically acceptable salt thereof, to the bovine upon the bovine's consumption of the animal feed. Premixes are recognized terms in the art for certain feed additives. They may be solid or liquid. A mineral premix is a composition which is intended for formation of an animal feed and which comprises desired kinds and amounts of minerals, in particular trace minerals. A vitamin premix is a composition which is intended for formation of an animal feed and which comprises desired kinds and amounts of vitamins. Some premixes include both vitamins and minerals. As such, feed additives includes premixes such as mineral premixes, vitamin premixes, and premixes which include both vitamins and minerals.

In some embodiments, lubabegron, or a physiologically acceptable salt thereof, is administrated to the bovine up to at least 91 days prior to slaughter of the bovine. In some embodiments, lubabegron, or a physiologically acceptable salt thereof, is administrated to the bovine up to at least 14 to 56 days prior to slaughter of the bovine. In some embodiments, the period of administration ends upon the bovine's slaughter. In another embodiment, the bovine is orally administered lubabegron, or a physiologically acceptable salt thereof, in daily feed rations up to 91 days prior to slaughter.

The term "effective amount", in the context of administration, refers to the quantity of lubabegron, or a physiologically acceptable salt thereof, when administered to a bovine, which is sufficient to reduce ammonia and/or carbon dioxide emissions from the bovine, as compared to a bovine untreated with lubabegron, or a physiologically acceptable salt thereof. The term "effective amount", in the context of a feed additive, refers to the quantity of lubabegron, or a physiologically acceptable salt thereof, included in the animal feed sufficient to reduce ammonia and/or carbon dioxide emissions from a bovine, as compared to a bovine untreated with lubabegron, or a physiologically acceptable salt thereof, when the bovine consumes the animal feed.

In some embodiments, lubabegron, or the equivalent of the lubabegron free base of a physiologically acceptable salt thereof, is administered in an amount from about 1 mg/day to about 500 mg/day. In some embodiments, lubabegron, or the equivalent of the lubabegron free base of a physiologically acceptable salt thereof, is administered in an amount from about 5 mg/day to about 500 mg/day. In some embodiments, lubabegron, or the equivalent of the lubabegron free base of a physiologically acceptable salt thereof, is administered in an amount from about 10 mg/day to about 400 mg/day.

In some embodiments, the animal feed contains from about 0.5 to about 100 grams of lubabegron, or the equivalent of the lubabegron free base of a physiologically acceptable salt thereof, per ton of animal feed. In some embodiments, the animal feed contains from about 0.5 to about 50 grams of lubabegron, or the equivalent of the lubabegron free base of physiologically acceptable salt thereof, per ton of animal feed. In some embodiments, the animal feed contains from about 1 to about 25 grams of lubabegron, or the equivalent of the lubabegron free base of a physiologically acceptable salt thereof, per ton of animal feed. In some embodiments, the animal feed contains from about 1.25 to about 20 grams of lubabegron, or the equivalent of the lubabegron free base of a physiologically acceptable salt thereof, per ton of animal feed.

In some embodiments, the present disclosure includes the use or inclusion of additional active ingredients. In some embodiments, the additional active ingredients are one or more selected from the group consisting of monensin, tylosin, and melengestrol, or physiologically acceptable salts thereof.

The terms and phrases in the Example have their ordinary meaning as understood by one of ordinary skill in the art.

EXAMPLE 1, REDUCTION OF AMMONIA EMISSIONS

Prepare lubabegron (L) as 4.5 g/lb of Type A Medicated Article. In a facility having at least eight cattle pen enclosures (CPEs), test two cycles of cattle, each cycle representing all dose (0, 1.25, 5, and 20 g/ton) and gender (steer and heifer) combinations. For the purpose of this example, a cycle refers to a group of 112 animals housed concurrently. Within each cycle, there are 2 cohorts of animals (56 animals per cohort). A cohort refers to a group of same gender animals representing each of the 4 doses. Up to 4 cycles are used to provide a total of 4 cohorts per gender.

Upon receipt of the cattle, allocate the cattle to CPEs to acclimate for 7 days. After the acclimation phase, for 91 days orally treat via feed one fourth of the cattle allocated to CPEs L 0 g/ton/day; one fourth 1.25 g/ton/day; 5 g/ton/day; and 20 g/ton/day (100% dry matter basis). Provide feed and water ad libitum. On day 91, collect body weight and load cattle for transport to the slaughter facility. On day 92, slaughter the cattle and evaluate the carcass. During the study, monitor and collect ammonia gas emissions data. Measure the ammonia emissions over the treatment period and normalize by body weight (BW) for the period (Days 0-7, 0-14, 0-28, 0-56, and 0-91) and hot carcass weight (HCW) (Days 0-91) (g of gas/animal; g of gas/lb of live BW; g of gas/lb of HCW). Using the process described above, the following results are achieved.

| Reduction, as compared to control | g of NH$_3$ gas/lb of live BW (g of NH$_3$ gas/animal) | | | | | g of NH$_3$ gas/ lb of HCW |
|---|---|---|---|---|---|---|
| Day | 0-7 | 0-14 | 0-28 | 0-56 | 0-91 | 0-91 |
| 1.25 g/ton | 5% (5%) | 14% (12%) | 16% (15%) | 13% (11%) | 11% (9%) | 13% |
| 5 g/ton | 8% (7%) | 17% (16%) | 21% (20%) | 18% (16%) | 14% (12%) | 16% |
| 20 g/ton | 22% (21%) | 27% (27%) | 26% (25%) | 19% (19%) | 15% (13%) | 17% |

EXAMPLE 2, REDUCTION OF CARBON DIOXIDE EMISSIONS

Prepare lubabegron (L) as 4.5 g/lb of Type A Medicated Article. In an appropriate facility having cattle chambers or rooms for individual animals (chambers), test ten cycles of twelve cattle each, each cycle representing all dose (0, 1.25, 5, and 20 g/ton) with a mixture of genders (steer and heifer).

Upon receipt of the cattle, allocate the cattle to chambers to acclimate for 7 days. After the acclimation phase, for 14 days orally treat via feed one fourth of the cattle allocated to chambers L 0 g/ton/day; one fourth 1.25 g/ton/day; 5 g/ton/day; and 20 g/ton/day (100% dry matter basis). Provide feed and water ad libitum. On day 14, collect body weight and load cattle for transport to the slaughter facility. On day 15, slaughter the cattle and evaluate the carcass. During the study, monitor and collect carbon dioxide gas emissions data. Measure the carbon dioxide emissions over the treatment period and normalize by body weight (BW) for the periods (Days 0-7, 0-14, and 7-14) and hot carcass weight (HCW) (Days 0-14) (g of gas/animal; g of gas/lb of live BW; g of gas/lb of HCW). Using the process described above, the following results are achieved.

| | Reduction, as compared to control | | | | |
|---|---|---|---|---|---|
| | g of CO$_2$ gas/lb of live BW (g of CO$_2$ gas/animal) Day | | | g of CO$_2$ gas/lb of HCW | |
| | 0-7 | 0-14 | 7-14 | 0-14 | 7-14 |
| 1.25 g/ton | 0% (0.2%) | 2% (3%) | 5% (5%) | 4% | 6% |
| 5 g/ton | 3% (4%) | 6% (7%) | 9% (10%) | 7% | 10% |
| 20 g/ton | 4% (4%) | 6% (7%) | 9% (9%) | 7% | 10% |

We claim:

1. A method of reducing one or more gas emissions selected from the group consisting of ammonia and carbon dioxide from a bovine comprising administering to said bovine lubabegron, or a physiologically acceptable salt thereof, wherein the method increases bovine hot carcass weight.

2. The method of claim 1, wherein the physiologically acceptable salt of lubabegron is the hemifumarate salt of lubabegron.

3. The method of claim 1, wherein one or more other active ingredients are administered to said bovine, wherein said other active ingredients are one or more selected from the group consisting of monensin, tylosin, and melengestrol, or physiologically acceptable salts thereof.

4. The method of claim 1, wherein said bovine is a cow.

5. The method of claim 1, wherein said reduction is per pound of the weight of the bovine while still alive.

6. The method of claim 1, wherein said reduction is per pound of hot carcass weight of said bovine.

* * * * *